(12) United States Patent
Biedermann et al.

(10) Patent No.: US 9,149,300 B2
(45) Date of Patent: Oct. 6, 2015

(54) BONE ANCHORING DEVICE

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/272,353

(22) Filed: May 7, 2014

(65) Prior Publication Data

US 2014/0330323 A1 Nov. 6, 2014

Related U.S. Application Data

(63) Continuation of application No. 12/890,341, filed on Sep. 24, 2010, now Pat. No. 8,764,810.

(60) Provisional application No. 61/245,940, filed on Sep. 25, 2009.

(30) Foreign Application Priority Data

Sep. 25, 2009 (EP) .................................... 09171416

(51) Int. Cl.
*A61B 17/04* (2006.01)
*A61B 17/86* (2006.01)
*A61F 2/08* (2006.01)
*A61B 17/70* (2006.01)

(52) U.S. Cl.
CPC ......... *A61B 17/7037* (2013.01); *A61B 17/7032* (2013.01); *A61B 17/8605* (2013.01)

(58) Field of Classification Search
USPC .................................................. 606/305–307
See application file for complete search history.

(56) References Cited

U.S. PATENT DOCUMENTS 5,716,356 A 2/1998 Biedermann et al.
6,485,491 B1 11/2002 Farris et al.
(Continued)

FOREIGN PATENT DOCUMENTS

CN 101185587 A 5/2008
CN 101237830 A 8/2008
(Continued)

OTHER PUBLICATIONS

Partial European Search Report for Application No. EP 09171416, dated Dec. 11, 2009, 4 pages.
(Continued)

*Primary Examiner* — Sameh Boles
(74) *Attorney, Agent, or Firm* — Christie, Parker & Hale, LLP

(57) ABSTRACT

A bone anchoring device includes an anchoring element having a shaft and a head; a receiving part for receiving the head and a rod, the receiving part being formed in one piece and having a top end and a bottom end, a bore extending from the top end to the bottom end, an inner wall defined by the bore, a substantially U-shaped channel adjacent to the top end for receiving the rod and a seat adjacent to the bottom end for accommodating the head; a pressure element; and a spring element having a spring force. The anchoring element is inserted from the top end and is pivotable with respect to the receiving part. The pressure element is movable in the bore so as to be able to fix the anchoring element at an angle with respect to the receiving part by exerting pressure onto the head. The spring element acts between the pressure element and the receiving part and allows the pressure element to be introduced from the top end but withstands against removal of the pressure element through the top end.

17 Claims, 7 Drawing Sheets

(56) References Cited

U.S. PATENT DOCUMENTS

| | | |
|---|---|---|
| 2004/0176766 A1 | 9/2004 | Shluzas |
| 2005/0080420 A1 | 4/2005 | Farris et al. |
| 2005/0283157 A1 | 12/2005 | Coates et al. |
| 2007/0288004 A1 | 12/2007 | Alvarez |
| 2008/0132957 A1 | 6/2008 | Matthis et al. |
| 2008/0154315 A1* | 6/2008 | Jackson .................. 606/309 |
| 2009/0069853 A1 | 3/2009 | Schumacher |

FOREIGN PATENT DOCUMENTS

| | | |
|---|---|---|
| DE | 10 2007 042 959 A1 | 3/2009 |
| EP | 1 459 690 A1 | 9/2004 |
| JP | 2007-14796 A | 1/2007 |
| WO | WO 02/22030 A2 | 3/2002 |
| WO | WO 03/068083 A1 | 8/2003 |
| WO | WO 2005/018471 A1 | 3/2005 |
| WO | WO 2005/046492 A1 | 5/2005 |
| WO | WO 2006/116437 A2 | 11/2006 |
| WO | WO 2006/135770 A2 | 12/2006 |
| WO | WO 2008/112114 A1 | 9/2008 |

OTHER PUBLICATIONS

European Search Report for Application No. EP 09171416, dated Jan. 29, 2010, 8 pages.

* cited by examiner

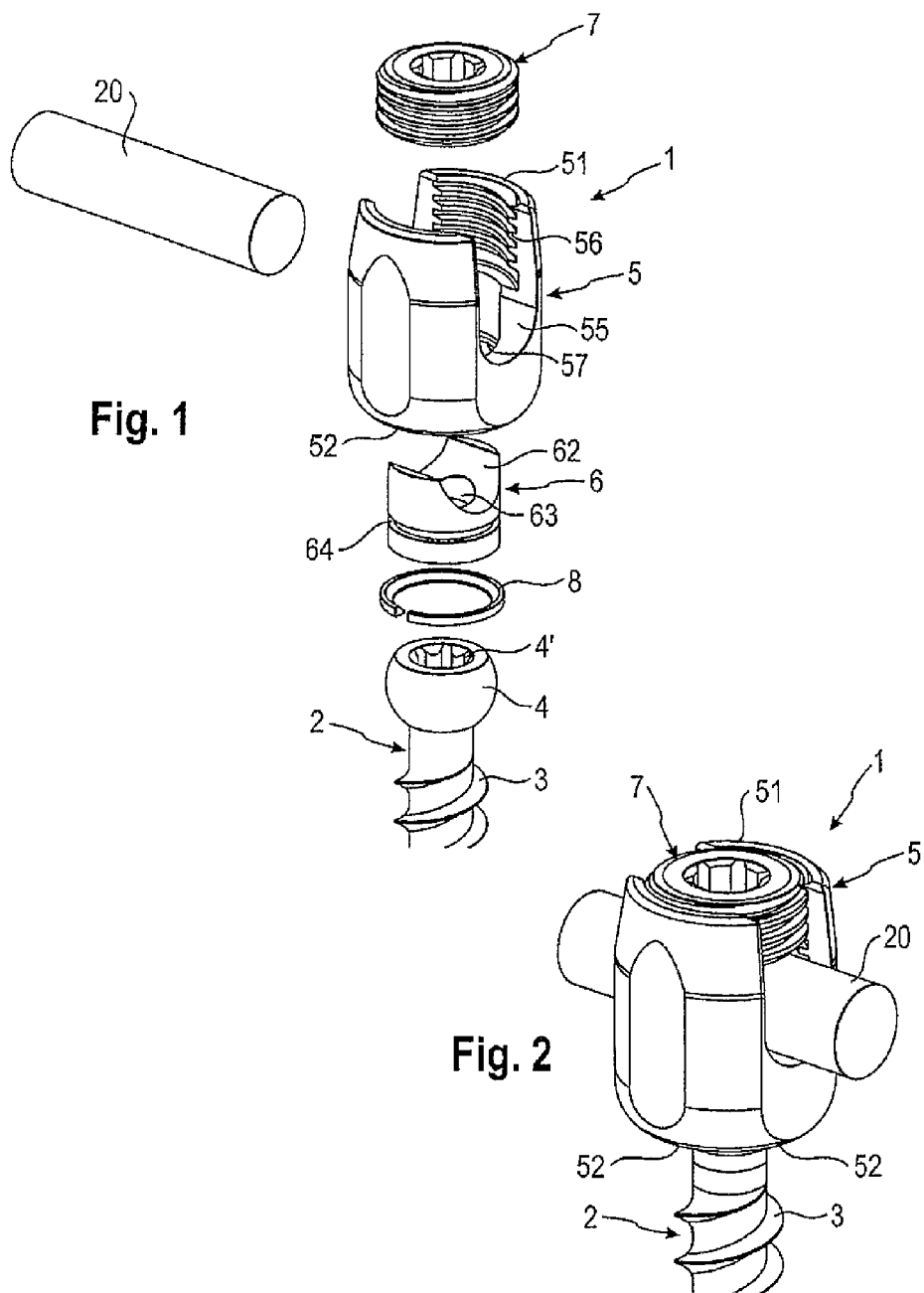

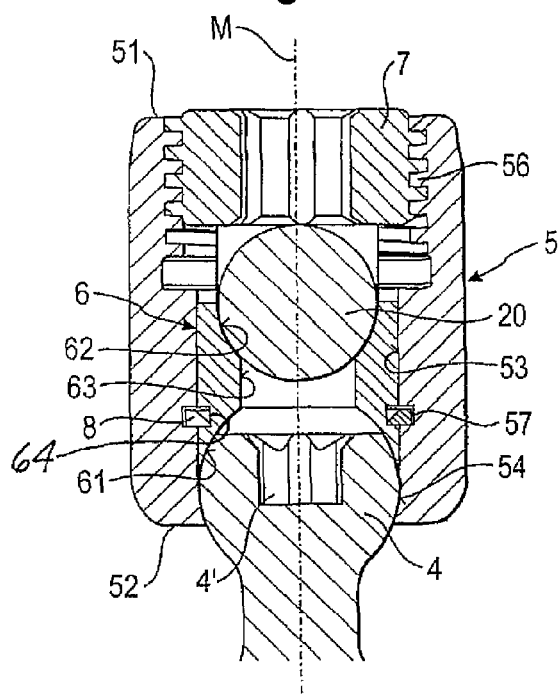
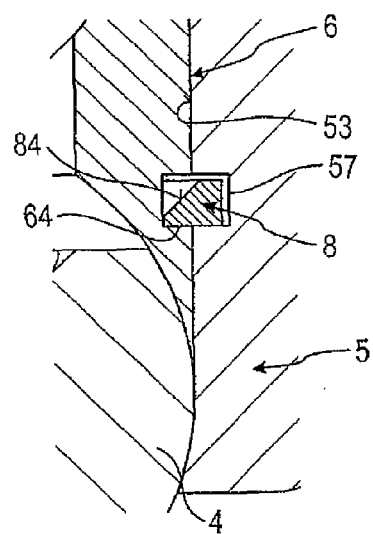

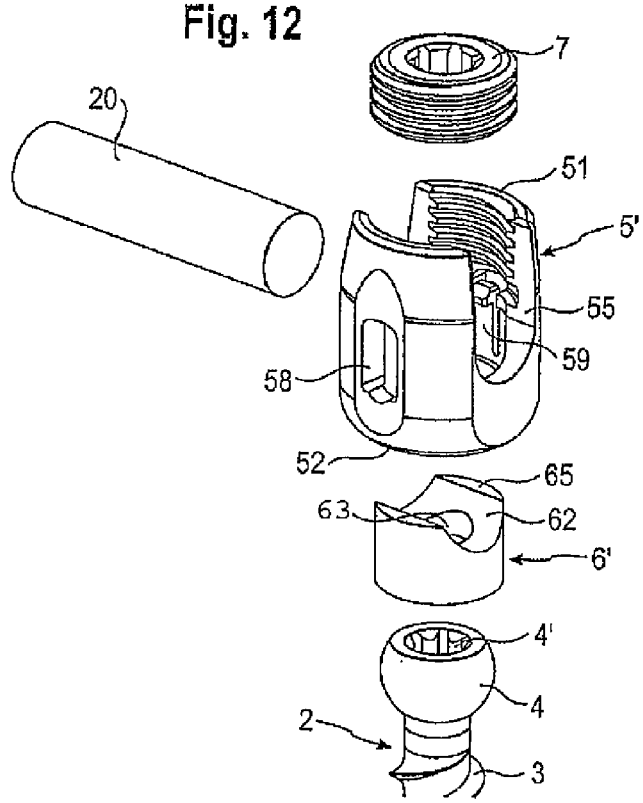
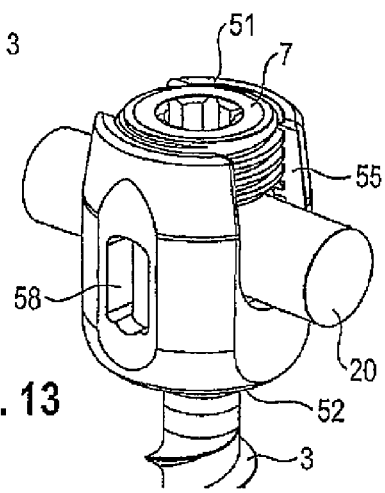

BONE ANCHORING DEVICE

CROSS-REFERENCE TO RELATED APPLICATIONS

This application is a continuation of U.S. patent application Ser. No. 12/890,341, filed Sep. 24, 2010, now U.S. Pat. No. 8,764,810, which claims priority to and the benefit of U.S. Provisional Patent Application Ser. No. 61/245,940, filed Sep. 25, 2009, and claims priority from European Patent Application Number EP09171416.2, filed Sep. 25, 2009, the entire contents of which are incorporated herein by reference.

BACKGROUND

The invention relates to a bone anchoring device for anchoring a stabilization rod in a bone or in a vertebra. The bone anchoring device includes an anchoring element, a receiving part for receiving a head of the bone anchoring element and for receiving a stabilization rod to be connected to the anchoring element. The anchoring element is pivotably connected to the receiving part and can be fixed at an angle by exerting pressure onto the head via a pressure element that is arranged in the receiving part. The anchoring element and the pressure element are to be inserted from a top end of the receiving part and a spring element withstands against removal of the pressure element through the top end once the pressure element is inserted.

U.S. Pat. No. 5,716,356 describes a polyaxial bone screw including a screw element and a receiving part that is pivotably connected to the screw element and a pressure element to exert pressure onto the head of the screw element to fix the angle between the screw element and the receiving part. The receiving part as an U-shaped channel for receiving a stabilization rod. The pressure element comprises a cylindrical recess that is to be aligned with the U-shaped channel to receive the rod therein. In order to hold the pressure element in a position aligned with the U-shaped channel, the position of the pressure element is fixed by crimping through bores provided in the receiving part.

US 2005/0080420 A1 describes a multi-axial bone screw that includes a screw element and a receiver member, a base member for retaining the screw element in the receiver member and a crown element exerting pressure onto the head of the screw element. The crown element comprises a snap-ring assisting in holding the crown element within the receiving part by interfering with a stop surface of the receiving part. The multi-axial bone screw is a so-called bottom loading type screw wherein the screw element is introduced from the bottom into the receiving part.

WO 2006/116437 A2 describes a bone anchor for spinal fixation in form of a polyaxial bone screw including a screw element, a housing, a sleeve and a collet arranged in the housing for exerting pressure onto the head of the screw element. The head of the screw element is introduced through the bottom of the housing. The sleeve has retention tabs that snap into slots in opposite wall portions of the housing. Alternatively, the retention tabs may be formed on the housing and the slots may be formed on the sleeve.

Usually, the polyaxial bone screws of the above described type are delivered, for example by the manufacturer, in a pre-assembled condition. In this condition a specific screw element, e.g. a screw element having a specific length and shaft diameter of a specific thread form, is connected to receiving part and the pressure element is arranged therein so that it can not escape. For the surgery, the necessary number and types of such pre-assembled polyaxial bone screws are selected and provided in advance as a full set of implants.

When the known polyaxial bone screws are in the pre-assembled condition, the pressure element is in a position that enables the head to freely pivot within the receiving part. In certain situations during surgery such an unrestrained pivoting is not desirable.

SUMMARY

It is the object of the invention to provide a bone anchoring device wherein parts can be selected and assembled by the surgeon or by any other personnel in a simple manner at the operation site or at any other place after the parts have been manufactured. In addition, the bone anchoring device shall provide an improved handling during surgery.

The bone anchoring device has only few parts. The parts are of a simple design. This provides for a lower cost manufacturing and a convenient handling. It is possible to assemble the bone anchoring device in any condition of the delivery after the parts have been manufactured and before the screw element is inserted into the bone. Therefore, the assembling of the polyaxial bone screw can be carried out by anybody, in particular by the surgeon or any personnel assisting him or her before or during surgery.

With the bone anchoring device a modular system can be provided, which allows the combination of various anchoring elements with any suitable receiver on demand, depending on the actual clinical requirements. This reduces the costs of polyaxial screws, reduces the inventory and gives the surgeon a substantial choice of implants. In addition, existing receiving parts may be upgraded to form the bone anchoring device according to the invention.

With the bone anchoring device it is possible to exert a slight biasing force onto the head of the screw element in the pre-assembled condition, so that a force, which can be applied by hand, for example, is needed to pivot the head. In certain situations, this improves the handling of the bone anchoring device during surgery. Different pressure elements can be provided so that the degree of biasing the pressure element against the head can be selected by selecting an appropriate pressure element when assembling the bone anchoring device.

Further features and advantages of the invention will become apparent from the description of embodiments by means of the accompanying drawings.

BRIEF DESCRIPTION OF THE DRAWINGS

FIG. 1 shows a perspective side view of a first embodiment of the bone anchoring device.

FIG. 2 shows a perspective side view of the bone anchoring device of FIG. 1 in an assembled state.

FIG. 3 shows a sectional view of the bone anchoring device of FIG. 2, the section being taken perpendicular to the rod axis.

FIG. 4 shows an enlarged view of a portion of FIG. 3.

FIG. 12 shows a perspective exploded view of a bone anchoring device according to a second embodiment.

FIG. 13 shows a perspective side view of the bone anchoring device of FIG. 12 in an assembled state.

DETAILED DESCRIPTION

Figure 5:
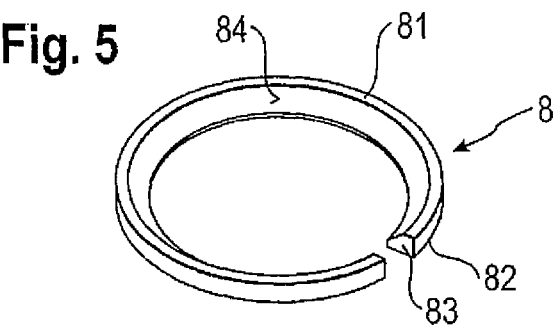
FIG. 5 shows a perspective view of the snap-ring of the first embodiment.

The bone anchoring device 1 according to a first embodiment shown in FIGS. 1 to 4 includes a bone anchoring element, in this case a screw member 2 having a threaded shaft 3 and a head 4. The head 4 is, for example, shaped as a spherical segment. The head 4 has a recess 4' at its free end for engagement with a tool. The bone anchoring device 1 further includes a receiving part 5 for connecting the screw member 2 to a rod 20. A pressure element 6 is arranged in the receiving part 5 on top of the head 4. For securing the rod 20 in the receiving part 5 and for exerting pressure onto the pressure element 6, a locking device in form of an inner screw 7 is provided. It should be understood that the locking device shown is exemplary and can be realized in many other designs, in particular as a two-part locking device and with different thread form. In addition, a spring element is provided in the form of snap-ring 8, which serves for holding the pressure element 6 within the receiving part 5.

The receiving part 5, as shown in particular in FIGS. 1 to 3, is formed in one piece. In the example shown, it is substantially cylindrical. It has a top end 51 and a bottom end 52 and a plane of symmetry M. A coaxial bore 53 extends from the top end 51 to the bottom end 52. The diameter of the bore 53 becomes smaller towards the bottom end 52, thereby providing a seat 54 for accommodating the screw head 4. The shape of the seat 54 can be spherical, conical or otherwise tapering. It can have any other shape that allows to accommodate the head 4 so that it can pivot with respect to the receiving part 5. The diameter of the bore 53 at the bottom end is sized such that the threaded shaft 3 can pass therethrough. The diameter of the bore 53 in the middle portion and until the top end 51 is sized such that the threaded shaft 3 and the head 4 of the screw element 2 can pass therethrough. At the top end 51, the receiving part has a substantially U-shaped recess 55 by means of which a channel is formed for receiving the rod 20. An internal thread 56 is provided near the top end 51 for cooperating with the inner screw 7 of the locking device.

The pressure element 6 is formed in one piece. It is of substantially cylindrical design construction and has an outer diameter that allows it to be inserted from the top end 51 and to be moved in axial direction within the coaxial bore 53 of the receiving part 5. On its side facing the head 4 of the screw element 2, a spherical recess 61 is provided that is adapted to the size of the head 4. Any other shapes of the underside of the pressure element 6 are conceivable, such as a flat surface or any other structure, however, a surface that is adapted to the head 4 of the screw element 2 provides a homogenous load distribution onto the head 4. On its side opposite to the head 4, the pressure element 6 has a cylindrical recess 62 adapted to receive the rod 20 therein. By means of this recess 62, a channel to receive the rod is formed. In the embodiment shown, the depth of the recess 62 is smaller than the diameter of the rod so that the inner screw 7 can come into contact with the rod 20. A coaxial bore 63 extends through the pressure element to allow access to the recess 4' with a tool for screwing-in the screw element 2.

The pressure element 6 further comprises a circumferential groove 64 that is provided in a portion of the outer surface of the pressure element below the cylindrical recess 62. The cross-section of the groove 64 is rectangular, however, it can also be square-shaped or can have rounded corners. It can also have another shape, for example, it can be asymmetric. The diameter of the groove 64 is such that it can accommodate a portion of the snap-ring 8. By means of the slot 83, the snap ring is resilient and can vary in its diameter.

The receiving part 5 comprises a corresponding circumferential groove 57, which is located below the bottom of the channel 55 so that when the snap-ring 8 is inserted, it is located below the rod 20. The groove 57 is sized so as to allow accommodation of a portion of the snap-ring 8. Like the groove 64 in the pressure element 6, the groove 57 in the receiving part 5 has a rectangular cross-section, a square-shaped cross-section or can have rounded corners. It can also have another shape, for example, it can be asymmetric.

Figure 6:
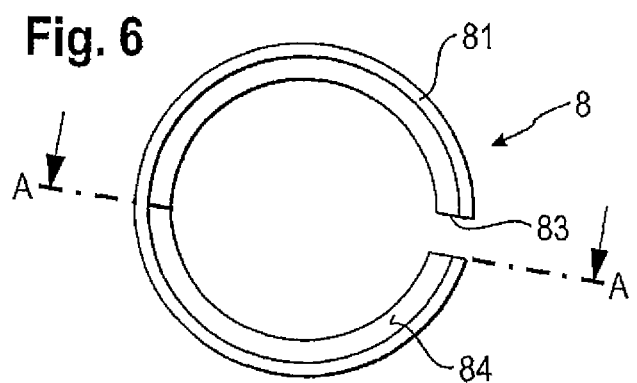
FIG. 6 shows a top view of the snap-ring of the first embodiment.
Figure 7:
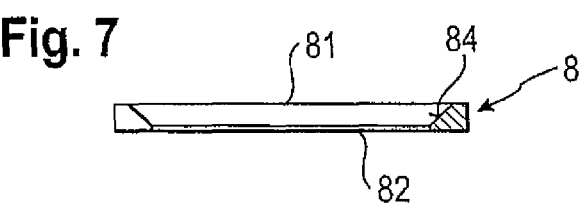
FIG. 7 shows a sectional view of the snap-ring of FIG. 6 along line A-A in FIG. 6.

The snap-ring 8 is described with reference to FIGS. 5 to 7. The snap-ring according to the first embodiment is circular. It has a top side 81, a bottom side 82 and a slot 83 extending completely through the snap-ring from the top side to the bottom side. The inner diameter of the snap-ring is smaller at the bottom side 82 than at the top side 81 and the cross-section of the snap-ring is substantially trapezoidal and an inclined surface 84 is formed on the top side 81. By means of this, the snap-ring is shaped asymmetrical in the direction of movement of the pressure element. The position of the groove 57 is such that when the snap-ring 8 is inserted in the groove 57 and the pressure element 6 is then inserted so that the snap-ring engages the groove 64 of the pressure element 6, the pressure element 6 is in a holding position that still allows pivoting of the head. The inner diameter of the snap-ring 8 is such that if the snap-ring is located in the groove 57, it can expand therein when the pressure element 6 is introduced until it snaps into the groove 64 of the pressure element.

The inner screw 7 of the locking device can be screwed into the internal thread 56 of the receiving part 5 until the inner screw 7 presses onto the upper side of the pressure element 6, which moves the pressure element 6 downward until it presses onto the head 4 to lock the head 4 in the receiving part 5.

The parts of the bone anchoring device are all made of a body-compatible material, such as titanium or stainless steel, a body-compatible metal alloy, for example a Ti—Ni alloy, or a body-compatible plastic material, such as PEEK. In particular, the snap-ring 8 can be made of a body-compatible plastic material that allows for an easy manufacture and a safe function of the spring element.

Figure 8:
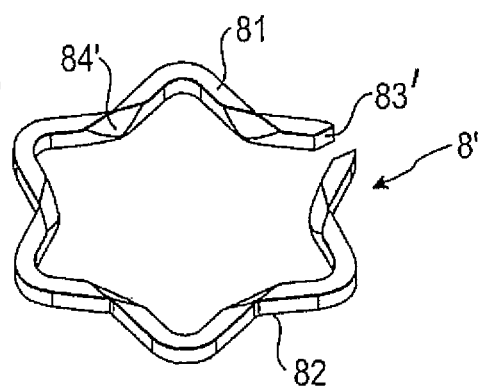
FIG. 8 shows a perspective view of a modified embodiment of the snap-ring.

FIG. 8 shows a modified example of a snap-ring 8'. A snap-ring 8' is not circular but has the shape of a star. It also has a slot 83' and inclined surfaces 84' that are preferably located in the valleys between the peaks of the star. The star-shaped snap-ring 8' can be made more flexible than the circular snap-ring 8. Other shapes are also conceivable, for example other wave-shaped rings with peaks and valleys.

In a further modification, the cross-section of the snap-ring can be symmetric in the direction of insertion and the cross-section of the grooves can be asymmetric.

Figure 9:
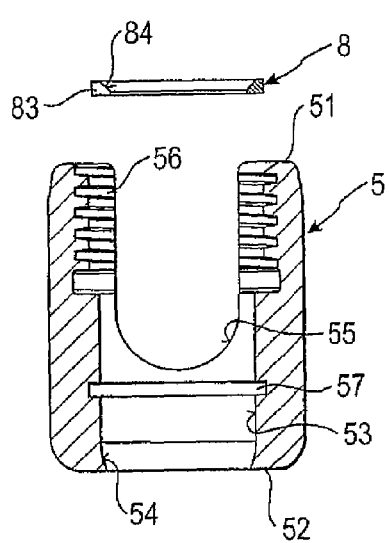
FIGS. 9-11 show steps of assembling the bone anchoring device according to the first embodiment in a sectional view, respectively.
Figure 10:
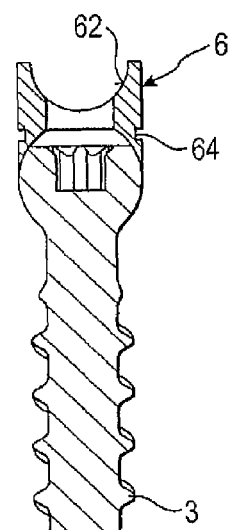
Figure 11:
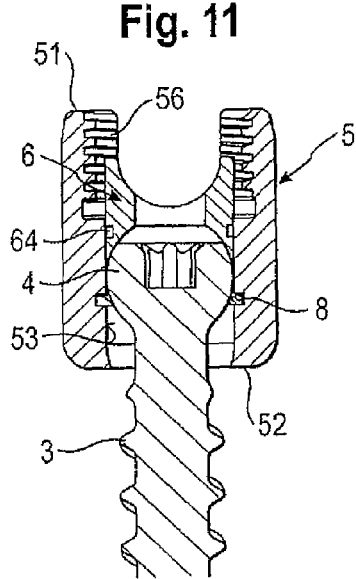
Figure 14:
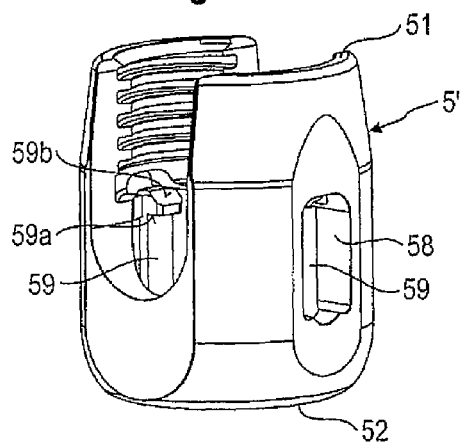
FIG. 14 shows a perspective view of the receiving part of the second embodiment according to FIGS. 12 and 13.
Figure 15:
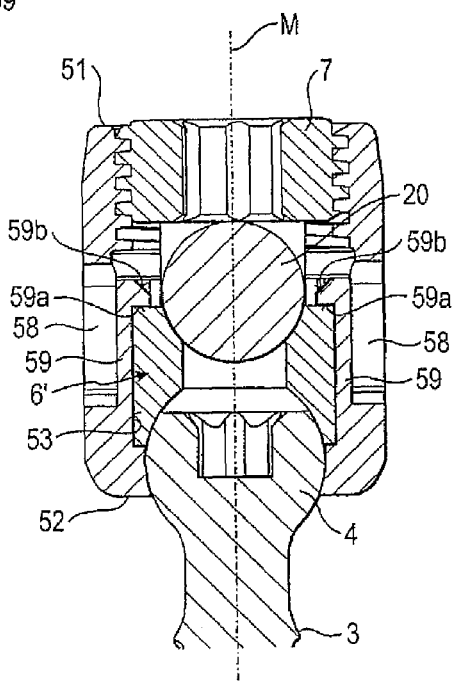
FIG. 15 shows a sectional view of the bone anchoring device according to the second embodiment of FIG. 13 in a sectional view, the section being taken perpendicular to the rod axis.
Figure 16:
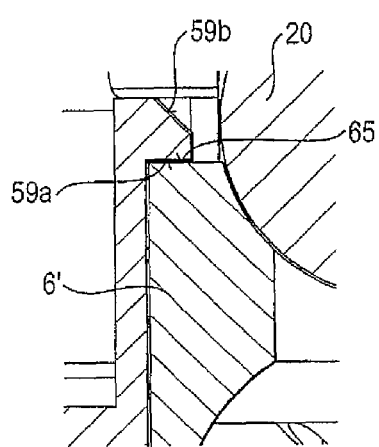
FIG. 16 shows an enlarged view of a portion of the bone anchoring device of FIG. 15.

FIGS. 9 to 11 show the steps of assembly of the bone anchoring device. In a first step, shown in FIG. 9, the snap-ring 8 is introduced into the receiving part 5 until it rests in the groove 57. The orientation of the snap-ring 8 is such that the inclined surface 84 faces the top end 51 of the receiving part 5. The orientation of the snap-ring 8 in a circumferential direction is such that the slot 83 can be positioned at around 90° with respect to the longitudinal axis of the channel 55.

In a next step, as shown in FIG. 10, the screw element 2 and the pressure element 6 are inserted into the receiving part 5 from the top end 51, so that the threaded shaft 3 passes through the bore 53 at the second end 52.

Then, as shown in FIG. 11, the pressure element 6 and the head 4 are moved downward toward the second end 52, thereby passing the snap-ring 8 that projects radially into the bore 53. Since the inclined surface 84 faces the top end 51 of the receiving part, the insertion force for the screw head 4 and the pressure element 6 is reduced. The screw head 4 and a lower edge of the pressure element 6 slide along the inclined surface 84, thereby expanding the snap-ring 8. The pressure element 6 is pushed downwards until the snap-ring 8 snaps into the groove 64 of the pressure element 6. Once the snap-ring is accommodated in the groove 64, the force necessary for removing the pressure element 6, i.e. removing the snap-ring from the groove 64, is increased since the upper part of the grooves 64, 57 act as a stop. Therefore, the pressure element 6 cannot fall out and can not be removed through the first end 51 without using a specific tool. Hence, the assembly of the pressure element 6 and the screw element 2 is unidirectional.

The position of the snap-ring 8 can be selected such that the pressure element 6 exerts a slight biasing force onto the head 4 in the pre-assembled condition. In this way, different pressure elements, for example, a first pressure element with a groove that is located higher than that of a second pressure element can be provided. When assembling the bone anchoring device, the appropriate pressure element to have a desired amount of biasing force can be selected.

Receiving parts and pressure elements of existing polyaxial screws can be upgraded with the grooves and the snap-ring.

In use, after assembly of the bone anchoring device 1, the screw element 2 is inserted into the bone. Thereafter, the receiving part 5 is pivoted until it has the correct orientation to take up the rod 20. The rod 20, which connects several bone anchoring devices, is inserted and the inner screw 7 is tightened to move the pressure element 6 downward to clamp the head 4 such that it is locked. Simultaneously the rod 20 is fixed by the inner screw 7. Since the inclined surface 84 faces the first end 51, the force needed for further pressing down the pressure element 6 is small because the upper edge of the groove 64 of the pressure element 6 slides along the inclined surface 84.

A second embodiment is shown with respect to FIGS. 12-17. The second embodiment differs from the first embodiment in that the spring element is not provided as a snap-ring but is provided as a portion of a receiving part. The description of features of the second embodiment that are the same as features of the first embodiment is not repeated. A receiving part 5' has on its two opposite sides longitudinal recesses 58, in which resilient fingers 59 are arranged. The resilient fingers 59 extend from the bases of the recesses 58 that are facing the second end 52, in the direction of the first end 51 and are flexible in a direction into and out of the recesses 58, respectively. Hence, the recesses 58 provide a space for taking up the resilient fingers 59 when they are pressed outward by a pressure element 6'. At their end facing the first end, the fingers 59 have a stop surfaces 59a, respectively, extending substantially perpendicular to the plane M. On the opposite side of each stop surface 59a there is an inclined surface 59b that faces the first end 51. The surface 59b is inclined downward to provide a sliding face along which the pressure element 6' can slide. The inner diameter between the resilient fingers 59 in the region of the stop surface 59a is smaller than the outer diameter of the pressure element 6'.

The pressure element 6' is shaped like the pressure element 6 of the previous embodiment, however, without the groove 64. An upper side 65 of the pressure element 6' comes into contact with the stop surface 59a of the resilient fingers 59.

Figure 17:
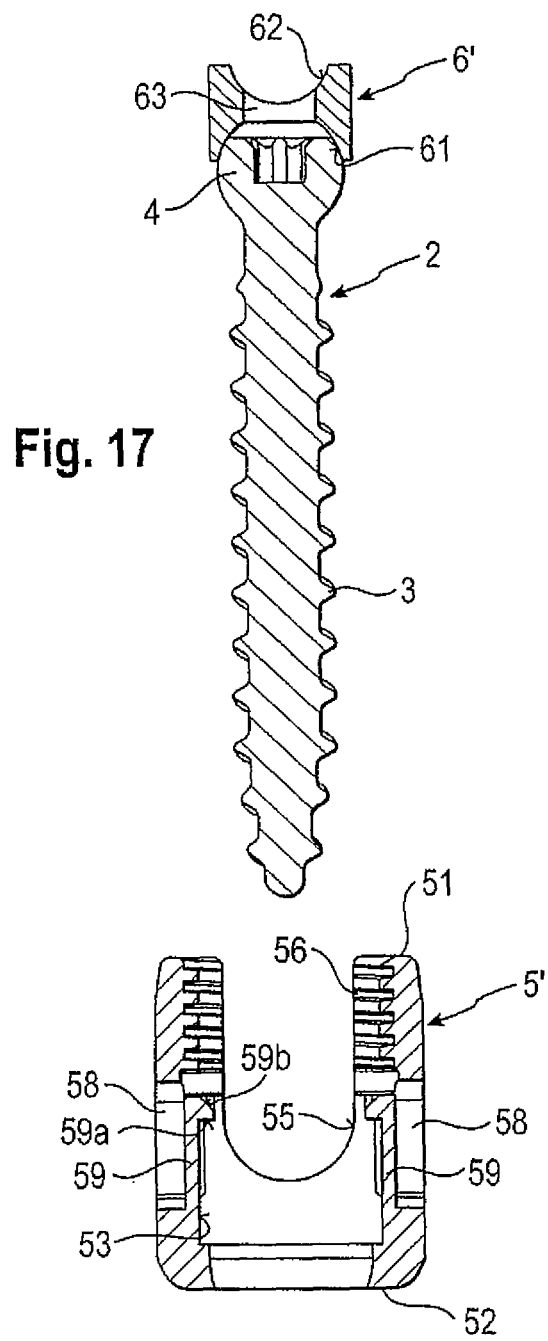
FIG. 17 shows the step of assembling the bone anchoring device according to the second embodiment.

The steps of assembly of the bone anchoring device according to the second embodiment include first providing the receiving part 5' and then inserting the screw element 2 with pressure element 6', as shown in FIG. 17, from the top end 51 of the receiving part 5'. The pressure element 6' and the head 4 are moved downward until the pressure element 6' contacts the inclined upper surface 59b of the resilient fingers 59, thereby pressing the resilient fingers 59 outward into the recesses 58 respectively. Since the inclined surface 59b faces the first end 51, the insertion force is small. When the pressure element 6' has passed the resilient fingers 59, the resilient fingers 59 snap back toward the bore 53 and removal of the pressure element 6' in the direction to the first end 51 is prevented by the stop surfaces 59a. Therefore, the assembly of the pressure element 6', the screw element 2 and the receiving part 5' is also unidirectional.

Further modifications of the embodiments are conceivable. For example, for the anchoring element, all kinds of anchoring elements can be used and combined with a receiving part. These anchoring elements are e.g. screws of different length, with different diameters, cannulated screws, screws with different thread forms, nails, etc.

All kinds of receiving parts can be used, in particular such with different locking elements, e.g. such as two-part locking devices that have an outer screw and an inner screw, which lock the rod and the head separately. In this case, the pressure element has a channel for the rod the depth of which is larger than the diameter of the rod. Other locking devices such as outer nuts, outer caps, bayonet locking devices or others are conceivable. The shape of the receiving part is not limited to the embodiments shown. For example, the receiving part can have an asymmetric end portion for allowing a greater pivot angle of the screw member to one side.

The shape of the pressure element is also not limited to the embodiments shown. For example, the pressure element can be designed so as to exert pressure onto the head from the side of the head, e.g. via a conically tapering portion and/or can have a slotted portion clamping the head or can have other shapes.

What is claimed is:

1. A bone anchoring device comprising:
 an anchoring element comprising a shaft for anchoring in the bone, and a head;
 a receiving part for receiving the head and for receiving a rod to be connected to the anchoring element, the receiving part being formed in one piece and having a top end and a bottom end, a bore extending from the top end to the bottom end, an inner wall defining the bore and forming a spring element having a spring force, a substantially U-shaped channel adjacent to the top end for receiving the rod, and a seat adjacent to the bottom end for accommodating the head, wherein the anchoring element is to be inserted from the top end; and
 a pressure element that is able to exert pressure onto the head, wherein the anchoring element is pivotable with respect to the receiving part and can be fixed at an angle by exerting pressure via the pressure element onto the head, wherein the spring element comprises a protrusion at a distal end that, in a relaxed state, extends into the bore, and wherein, a top surface of the protrusion facing the top end and a bottom surface of the pressure element are shaped such that, when the pressure element is inserted through the top end and contacts the protrusion, the spring element moves away from the bore to allow the pressure element to pass farther into the receiving part.

2. The bone anchoring device of claim 1, wherein the spring element is asymmetric in the direction of insertion.

3. The bone anchoring device of claim 1, wherein the spring element is designed such that the pressure element can be moved into a first holding position and a second holding position, wherein in the first holding position, the pressure element exerts a biasing force against the head sufficient to hold the anchoring element stationary with respect to the receiving part, yet still allow pivoting of the anchoring element when an external force is applied, and wherein in the second holding position, the pressure element locks the anchoring element with respect to the receiving part.

4. The bone anchoring device of claim 3, wherein the pressure element snaps into the first holding position against the spring force of the spring element.

5. The bone anchoring device of claim 1, wherein the spring element provides a stop surface such that, when a force is applied to the pressure element in a direction toward the top end, the spring element prevents removal of the pressure element through the top end.

6. The bone anchoring device of claim 1, wherein the pressure element is located in a pre-assembled condition at a position in which it exerts a slight biasing force against the head.

7. A modular system comprising the bone anchoring device according to claim 1, wherein a plurality of different shanks and/or a plurality of different heads are provided.

8. The bone anchoring device of claim 1, wherein, in the relaxed state, the spring element extends parallel to a longitudinal axis of the bore and the protrusion extends perpendicular to the longitudinal axis.

9. A bone anchoring device comprising:
an anchoring element comprising a shaft for anchoring in the bone, and a head;
a receiving part for receiving the head and for receiving a rod to be connected to the anchoring element, the receiving part being formed in one piece and having a top end and a bottom end, a bore extending from the top end to the bottom end, an inner wall defining the bore and forming a spring element having a spring force, a substantially U-shaped channel adjacent to the top end for receiving the rod, and a seat adjacent to the bottom end for accommodating the head, wherein the anchoring element is to be inserted from the top end; and
a pressure element that is able to exert pressure onto the head, wherein the anchoring element is pivotable with respect to the receiving part and can be fixed at an angle by exerting pressure via the pressure element onto the head, and wherein, in a first holding position in which the spring element engages and restrains movement of the pressure element, the pressure element exerts a biasing force against the head sufficient to hold the anchoring element stationary with respect to the receiving part, yet still allow pivoting of the anchoring element when an external force is applied before locking the head with respect to the receiving part.

10. The bone anchoring device of claim 9, wherein the spring element is formed by at least one elastic finger that can resiliently move into and out of a recess in the inner wall of the receiving part.

11. The bone anchoring device of claim 9, wherein the spring element is provided at a side wall of the channel.

12. The bone anchoring device of claim 9, wherein the spring element is asymmetric in the direction of insertion.

13. The bone anchoring device of claim 9, wherein the spring element is designed such that the pressure element can be moved from the first holding position to a second holding position,
and
wherein, in the second holding position, the pressure element locks the anchoring element with respect to the receiving part.

14. The bone anchoring device of claim 13, wherein the pressure element snaps into the first holding position against the spring force of the spring element.

15. The bone anchoring device of claim 9, wherein the spring element provides a stop surface such that, when a force is applied to the pressure element in a direction toward the top end, the spring element prevents removal of the pressure element through the top end.

16. The bone anchoring device of claim 15, wherein the stop surface is configured to contact a top surface of the pressure element.

17. The bone anchoring device of claim 9, wherein the spring element has an inclined surface that allows the pressure element to gradually move the spring element during insertion.

* * * * *